United States Patent [19]
Britton

[11] Patent Number: 5,853,372
[45] Date of Patent: Dec. 29, 1998

[54] NEAR INFRA-RED SIGNAL PROCESSING SYSTEM

[75] Inventor: Stuart D. Britton, San Diego, Calif.

[73] Assignee: Advanced Body Metrics Corporation, Rancho Santa Fe, Calif.

[21] Appl. No.: 515,047

[22] Filed: Aug. 14, 1995

[51] Int. Cl.[6] .................................................. A61B 5/00
[52] U.S. Cl. .......................................... 600/500; 600/485
[58] Field of Search ........................... 128/633, 4, 664–7, 128/672, 687, 690, 748; 600/310, 473–478, 485, 500, 503, 561

[56] References Cited

U.S. PATENT DOCUMENTS

| | | | |
|---|---|---|---|
| 5,278,627 | 1/1994 | Auyagi et al. | 128/633 |
| 5,297,548 | 3/1994 | Pologe | 128/633 |
| 5,431,170 | 7/1995 | Mathews | 128/687 |
| 5,533,507 | 7/1996 | Potratz | 128/633 |

*Primary Examiner*—Robert L. Nasser
*Attorney, Agent, or Firm*—G. Donald Weber, Jr.

[57] ABSTRACT

A signal processing system which utilizes a near infra-red sensor signal to monitor the heart pulse rate of a user. The signal processing system is used to control and monitor the output of the near infra-red sensor to which detects the rate of change of blood flow through arteries of the user. The system operates on the signal from the sensor to detect the pulse rate of the heart of the user. The system can be analog or digital in operation.

20 Claims, 1 Drawing Sheet

NEAR INFRA-RED SIGNAL PROCESSING SYSTEM

BACKGROUND

1. Field of the Invention.

This invention relates to heart pulse monitors, in general, and, more particularly, to a heart pulse monitor that is worn by the user, for example at the wrist, and is capable of accurate measurement and display of the user's heart pulse rate (and variation thereof) during physical exercise or other activity.

2. Prior Art.

Today, there is a substantial interest in physical well-being and exercising. In conjunction therewith, electronic equipment is employed by persons during athletic training for monitoring of a person's heart pulse activity. One important measurement parameter is the rate of occurrence of heart pulsations. In healthy persons, the pulse rate is substantially uniform throughout the duration of an activity. However, the rate may vary with changes in the person's activity. The rate of pulse change during increasing or decreasing activity is directly related to a person's physical condition. Thus, it will be appreciated that a device providing an accurate measurement of pulse rate is highly desirable.

One device useful for the measurement of heart pulse rate is an electronic unit worn on the wrist. In the past, this has necessitated the use of complex electronic equipment. That is, the accurate measurement of an active person's pulse rate at the wrist is a complex process due to the artifacts produced by body motion. These artifacts are concurrent with the heart pulse and are detected by the heart pulse sensor as noise. In many cases, this noise can produce signals of sufficient amplitude to completely mask the heart pulse signal which is to be measured. In order to mitigate the effects of these body artifacts, it is necessary to filter out and electrically cancel as much of the noise signal occurring in the heart pulse frequency band as possible while retaining the desired pulse signal. This problem must be dealt with effectively over a considerable signal-to-noise ratio range.

During monitoring sequences it is important that the user be able to receive accurate updates of heart pulse rate frequently. This is important even in situations where physical activity is creating body artifact noise in excess of what can be tolerated by the sensing system to provide an updated, accurate read-out of pulse rate.

Several devices have been proposed for providing a wristwatch type of heart pulse monitor. U.S. Pat. No. 4,120,269 (Prinz) describes one type of such device, viz. a digital plethysmography which customarily utilizes an infrared light transducer.

U.S. Pat. No. 4,059,118 (Stupay) describes a device which uses an actuator pin pressing against a piezoelectric crystal.

U.S. Pat. No. 4,224,948 (Cramer) describes a device which uses a piezoelectric sensor to obtain a pulse reading from the radial artery in the subpollex depression.

U.S. Pat. No. 4,409,983 (Albert) describes a complex arrangement of piezoelectric sensors to develop a relatively noise free signal which is presented to the input of a microprocessor.

U.S. Pat. No. 4,781,195 describes a device which uses an optical sensor sytstem for cancelling the ambient light signal in a blood oxygenization monitor mounted on the user's finger.

The known devices tend to have several shortcomings. Those devices using optical transducers, such as the digital plethysmographies, consume substantial power in the light emitting elements. Thus, use with a battery is not effective. Devices using piezo-electric transducers typically devote little attention to the substantial noise problems that attend the use of such transducers in this application.

When such a pulse rate monitor is mounted on the wearer's wrist, the pulse signal is, to a significant extent, masked by the concurrent noise signals generated due to body motions. The mechanical transducer responds both to pressure from the wearer's pulse beat and to motion from walking, arm swinging and the like, and does not distinguish between them. However, this response is noise insofar as pulse measurement is concerned. As the Stupay patent teaches, "the patient must remain quiet to avoid noise input" during the period in which the pulse rate is being measured.

Also, if the piezoelectric transducer is not mounted directly over the artery of the user, the pulse signal measured by the device will be significantly reduced in amplitude. Thus,the signal is even more likely to be masked by noise. Typically, noise signals may be as high as 1.0 volt, while the pulse signal may be approximately 0.1 volt. Consequently, prior art wrist watch pulse rate monitors employing piezo-electric transducers have been inaccurate because of this unfavorable signal-to-noise ratio.

Devices using optical sensors tend to not detect body transmitted acoustical noise. However, optical sensors used to detect the heart rate pulse at the radial artery on the wrist tend to have many of the same body motion related problems as the piezo sensor systems. Added to the motion induced noise problems is the introduction of noise artifacts that are caused by ambient light conditions. These noise sources can be any electrical or natural light sources, including the sun.

Absolute detection sensors (the latest known practice) have a difficult time subtracting out the voltage pedestal of the photo-diode. This pedestal represents 95–99% of the voltage with the last 1–5% representing the desired modulation. Removing this pedestal while maintaining voltage offsets and high gains requires complicated circuitry. An effective method of dealing with these noise sources is necessary in order to make accurate heart pulse rate readings while the body is in motion or exposed to changing lighting conditions.

COPENDING APPLICATIONS

HEART PULSE MONITOR; Bryars, Ser. No. 08/462,156, filed Jun. 5, 1995. (ABC-1(CONT)

HEART PULSE MONITOR; Bryars et al., Ser. No. 08512,712, filed Aug. 9, 1995. (ABC-1(CONT)(CIP)

PUMP BAND; Bryars, Ser. No. 08/174,266, filed Dec. 28, 1993 now U.S. Pat. No. 5,559,243 (ABC-4)

SUMMARY OF THE INSTANT INVENTION

This invention is directed to a signal processing system which uses a near infra-red sensor signal. One preferred use is in a heart pulse rate monitoring system. The sensor operates on the rate of change (derivative) of flow and produces digitized data representative thereof.

This approach effectively removes the voltage background (or ambient) of the photo-diode while allowing the modulation to be amplified at a high gain. Additionally, the LED current is adjustable allowing the system to consume only as much power as necessary to find the heart rate.

This approach permits the ready removal of all or substantially all of the background (or ambient) voltage of the optical sensing device and leaves the desired modulation signal substantially intact, without complicated circuitry requirements.

Power consumption is minimized by utilizing optimum duty-cycles and power management circuitry.

DESCRIPTION OF A PREFERRED EMBODIMENT

Figure 1:
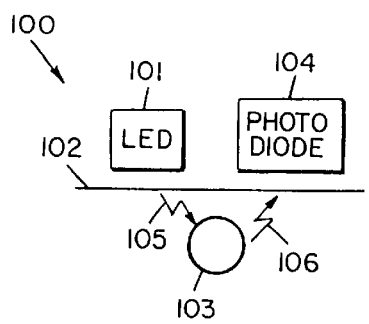
FIG. 1 is a simplified, schematic representation of an optical detector of blood flow at a detector-body interface.

Referring now to FIG. 1, there is shown a simplified schematic representation of a heart pulse rate detector 100 of the type described in the co-pending references noted above. The detector 100 is an optical detector.

In this embodiment, the illuminating device 101, for example a light emitting diode (LED), is disposed external to the user's skin (or body tissue) 102 in any suitable fashion. The LED is located adjacent to a blood vessel 103, for example an artery, which is below the skin 102. The LED 101 directs light 105 onto the vessel 103 through the tissue 102. A light detector 104, for example a photo-diode, is disposed external to the user's skin or adjacent to the blood vessel 103. The detector 104 is adapted to receive light 106 reflected from the vessel 103.

The circuitry associated with the detector 100 is omitted for clarity, as is the mounting structure and the like.

Figure 2:
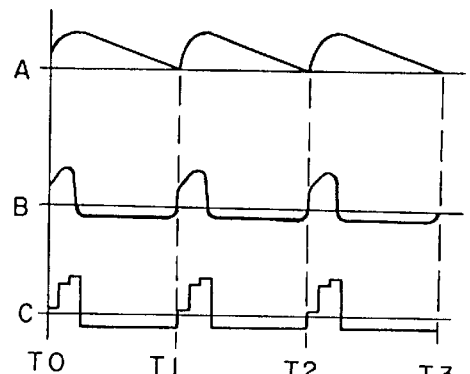
FIGS. 2A, 2B and 2C are graphic representations of blood low, rate of change of blood flow and a digitized representation thereof, respectively.

Referring now to FIG. 2, there is shown a graphic representation of the functional operation of the system of the instant invention. In particular, at FIG. 2A, there is shown a representation of blood flow through vessel 103 in FIG. 1. Though not limited thereto, vessel 103 is preferrably an artery. As is seen, upon contraction of the heart, a volume of blood is forced through the blood vessel. After a brief surge, the blood flow falls off at a fairly constant rate until the next contraction of the heart. At that time, the blood flow is repeated.

In FIG. 2B, there is shown the rate of change of the blood flow (or wavefront) through artery 6. The rate of change of blood flow is quite rapid at the beginning of a contraction of the heart. As noted, the blood flow then becomes fairly constant. Thus, the rate of change becomes nearly zero. Consequently, the rate of change (i.e. derivative) of blood flow produces a series of pulses which coincide with the contraction of the heart and the initial rapid flow of blood in the artery.

Shown in FIG. 2C is a digitized version of the derivative signal shown in FIG. 2B. The digitized signal approximates the derivative signal closely and has the same rate. This signal represents the heart pulse rate and is the signal which is detected/produced by the heart pulse rate monitors described in the copending references described above. The detector system of the instant invention produces the sensor output signal of FIG. 2C with substantial accuracy and reliability.

Figure 3:
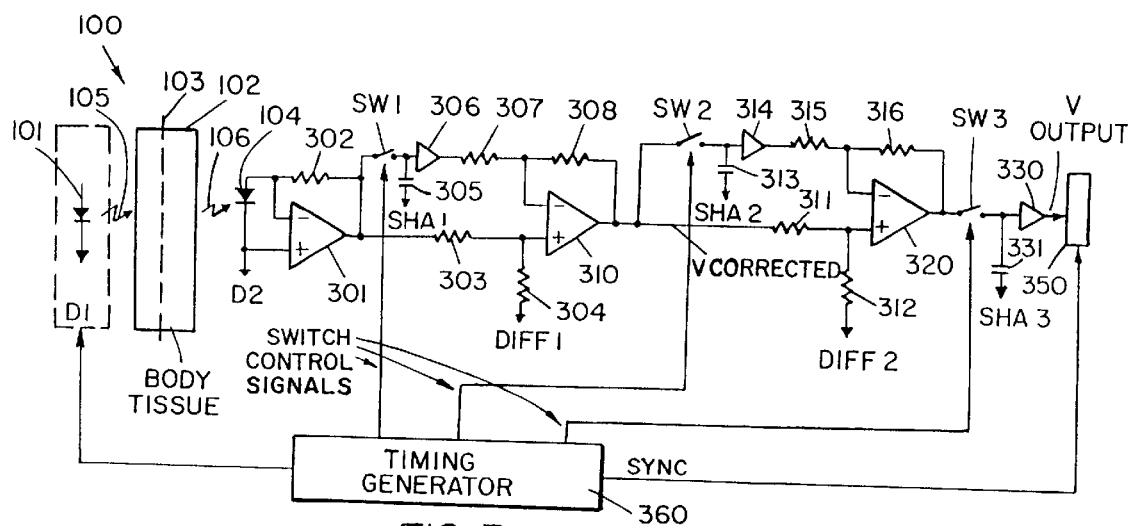
FIG. 3 is a schematic diagram of one embodiment of the signal processing system of the instant invention.

Referring now to FIG. 3, there is shown a schematic circuit diagram of the signal processing system of the instant invention. The detector 100 is similar to the simplistic detector 100 shown in FIG. 2. The LED 101, typically an infra-red (IR) LED, is driven by a pulsed current source (not shown) and shines light onto the body tissue 102 and the blood vessel 103. Light is reflected from the tissue and from the vessel 103. In this instance, the light reflected from the tissue 102 is, effectively, superimposed upon the ambient signal. The light reflected from the vessel 103 varies as a function of the amount of blood passing through the vessel 103. The light from source 101 is, typically, absorbed by the blood in the vessel 103. Consequently, an "empty" vessel reflects more light than a "full" vessel. Thus, as a blood wavefront passes, the light reflected from the vessel changes and produces a pulse similar to the pulse shown in FIG. 2.

However, the ambient signal, including the light reflected from the tissue 102, is quite large (on the order of a volt or more). On the other hand, the signal produced by the light reflected from the vessel 103 is quite small (on the order of 10 millivolts). The variable signal which represents the light reflected by the vessel 103 must be separated from the ambient signal (which also may vary).

The photodetector 104, typically a photo-diode, is activated by the light (ambient and/or signal) applied thereto and generates a current therethrough. The photo-diode current signal is applied to the input terminals of a conventional transimpedience amplifier 301 (including feedback path 302) and produces an output voltage. The output voltage from the amplifier 301 in response to the signal from photo-diode 108 is shown as Vbackground (or ambient) and Vpedestal (ambient plus signal) as shown in FIG. 5B.

The output voltage produced by amplifier 301 is supplied to one input of differential amplifier 310 via the voltage divider network comprising impedances 303 and 304, for example. Thus, the actual voltage supplied to the positive (+) input terminal of amplifier 310 is a function "k1" of the output voltage produced by amplifier 301 where k1 is determined by the relation of the impedances 303 and 304 of the voltage divider. The constant k1 can have any value greater than zero and up to one. The value of k1 is not important in the invention but is developed, in any specific embodiment, in conjunction with the other parameters of the system including the sample and hold circuit SHA1 and the amplifier 310 including the feedback network associated therewith.

In addition, the voltage produced by amplifier 301 is supplied to a sample and hold circuit SHA1. The circuit SHA1 includes a switch SW1 and a storage capacitor 305. Thus, when switch SW1 is closed, storage capacitor 305 is charged to a level determined by the output voltage from amplifier 301. The switch SW1 is then opened whereupon the voltage sample is held in the capacitor 305. This voltage level is supplied to the input of amplifier 306 and applied to a second (negative) input terminal of differential amplifier 310 via impedance 307 (along with the feedback voltage supplied via feedback impedance 308). The output voltage at the output terminal of amplifier 310 is the corrected pedestal voltage (V pedestal-V background) shown in FIG. 5B which is representative of the difference between the voltage levels supplied to the input terminals thereof.

The magnitude of Vpedestal relative to Vbackground is a function of several parameters including the amount of current (power) applied to the LED; the amount of shielding of the photo-diode; the degree of coupling between the LED and the photo-diode; as well as other factors involved in the design of the sensor system.

A function K2 of the corrected pedestal voltage is supplied from amplifier 310 to one input terminal of differential amplifier 320 via the voltage divider path comprising impedances 311 and 312 (where k2 is determined by the relation of impedances 311 and 312 similar to the determination of k1 as described supra. The corrected pedestal voltage is also supplied to the other (negative) input terminal of amplifier 320 via the sample and hold circuit SHA2. Sample and hold circuit SHA2 includes switch SW2, capacitor 313, amplifier 314 and impedance 315. Impedance 316 provides the feedback loop for differential amplifier 320.

The output terminal of differential amplifier 320 is connected to the utilization device 350 via sample and hold circuit SHA3. Sample and hold circuit SHA3 includes switch SW3, capacitor 331 and amplifier 330. Amplifier 330 produces the output voltage Vout which is representative of the modulated signal alone detected at the photo-diode 104. That is, the background induced voltage which represents all of the ambient signal (or noise) at the sensing location has been deleted from the pedestal voltage and only the active signal representative of the light reflected by the vessel 103 is presented as the output signal.

The timing generator 360 is used to control the sample rate. Sample periods of 1280 and 2560 system clock periods are selectable by the utilizing system. The timing generator is responsible for powering up different system elements as the usage approaches. Before a sample is taken, the system is powered up in order to detect the background signal. After the sample is complete, unnecessary electronics are powered down. All sample and hold circuits, analog to digital converters, (in the event a digital output is required) and the LED current source are controlled by signals from the timing generator.

Figure 4:
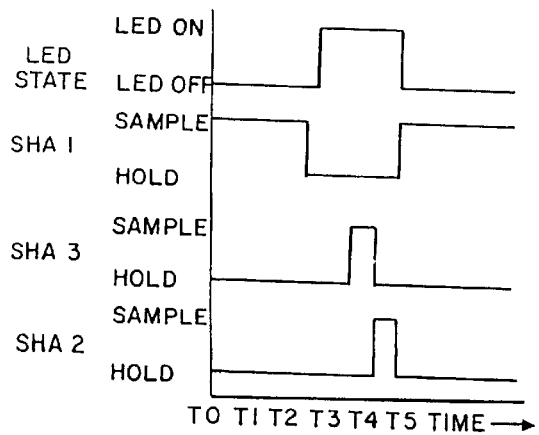
FIG. 4 is a timing diagram for the operation of the circuit shown in FIG. 3.
Figure 5:
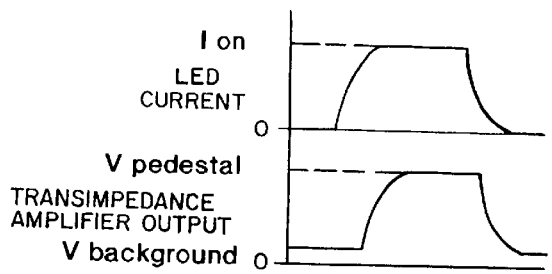
FIG. 5 is a graphic representation of the LED current and the transimpedance amplifier output.

In describing the operation of the embodiment of the invention shown and described relative to FIG. 3, reference is concurrently made to FIGS. 4 and 5.

As shown in FIG. 5, current is supplied to LED 101 by any suitable source (not shown). The LED current ramps up quickly from 0 to Ion, the maximum current through LED 101. This causes LED 101 to produce a light emission which is applied to the sensing or detecting site. The photo-diode 104 is activated by the light received thereby and produces a voltage. As shown in FIG. 5B, the photo-diode produces a voltage (referred to as Vbackground or Vambient). As previously described, this voltage can be on the order of 1 or 2 volts in some embodiments. This voltage can vary significantly unless special shielding precautions are taken relative to the photo-diode placement. When the LED 101 is energized or activated, the light produced thereby causes a voltage pulse to be produced by photo-diode 104 as suggested by FIG. 5B. However, the magnitude of the modulated voltage produced by light reflected from the artery 103 is quite small. As previously described, this voltage can be on the order of 10 millivolts. Because it is necessary to measure this modulated voltage, the ambient or background signal must be removed for accurate readings of the modulation.

The total voltage signal produced by the photo-diode 104 is applied across the input terminals of transimpedance amplifier 301. The output voltage (or a function thereof) produced by amplifier 301 is applied to respectively the sample and hold circuit SHA1 and to an input of differential amplifier 310. The timing circuit 360, as shown in FIG. 4, operates to close switch SW1 immediately prior to activating LED 101. Thus, circuit SHA1 samples and holds (i.e. tracks) the voltage level at the output of amplifier 301 at all times when the LED is not activated. The sample and hold circuit SHA1 thereby samples the voltage produced by amplifier 301 as a result of the background or ambient light at the detection site.

The background voltage at the sample and hold circuit SHA1 is applied to the negative input terminal of differential amplifier 310. The amplifier 310 operates to subtract the background signal supplied by the sample and hold circuit SHA1 from the signal supplied to amplifier 310 by the transimpedance amplifier 301 when the LED 101 is activated. The amplifier 310, thus, produces the background-corrected pedestal voltage which is the voltage signal produced by photo-diode 104 solely by the activation of LED 101.

A representative value of the corrected pedestal voltage, Vpedestal-Vbackground, is applied from amplifier 310 to one input terminal of differential amplifier 320 via the voltage divider input circuit. The corrected pedestal voltage is also supplied to the sample and hold circuit SHA2. In particular, when switch SW2 is closed, the corrected pedestal voltage is supplied across capacitor 313 and stored therein. The stored voltage is applied to the input of 314. The amplified voltage across capacitor 313 is applied to the negative terminal of differential amplifier 320 via impedance 315. Thus, the voltage on capacitor 313 is subtracted from the corrected pedestal voltage.

The output voltage produced by differential amplifier 320, which has a relatively large gain, is selectively supplied to sample and hold circuit SHA3. That is, when switch SW3 is closed, the output voltage produced by amplifier 320 is stored across capacitor 331 and amplified by amplifier 330. The output signal produced by amplifier 330 is referred to as Voutput and is supplied to the utilization device 350. The utilization device 350 will, typically, include a suitable display device for providing a visual readout of the heart pulse rate.

Typically, the utilization device 350 can include an analog-to-digital converter (ADC) and a digital signal processor; an ADC and a microprocessor, a level detector and time interval counter or the like. Of course, other suitable devices are contemplated for use in utilization device 350.

The timing control signals are provided by the timing generator 360. The control signals have the sequence shown in FIG. 4. The voltage difference betwen vpedestal and Vbackground is the desired starting point for the signal processing. To obtain the corrected Vpedestal, the Vbackground voltage is sampled immediately before the LED 101 is turned on and is fed to the negative input of a differential amplifier. The output of the differential amplifier is the desired Vpedestal-Vbackground signal for further processing. In this embodiment, the timing sequence begins at TO. The LED 101 is turned OFF and does not emit light. Sample and hold circuit SHA1 is turned ON so that the existing signal, whether from amplifier 301 or directly from the detection site (in the case where amplifier 301 is omitted), is sampled and stored. This operation permits the system to recognize the background signal (see FIG. 5B).

At time T1, the switch SW1 is opened whereby the sample and hold circuit SHA1 is placed in the "hold" mode and is disconnected from the detector 104.

Shortly thereafter, at time T2, the LED 101 is turned ON to produce the illumination on the photo-diode. When the LED is pulsed, the photo-diode sees the irradiation from the LED returned from the body. Some light is absorbed by the body and some light is reflected. A small percentage of the light reaches the artery and is modulated by the blood flow. FIG. 5 shows the LED current pulse and the output of the transimpedance amplifier. The signal produced by the photo-diode 104 is supplied to the transimpedance amplifier 301 which produces the output signal Vpedestal as shown in FIG. 5B. This signal is supplied to an input terminal of differential amplifier 310. via the voltage divider network comprising impedances 311 and 312 as described supra. The signal at sample and hold cirucit SHA1 is applied to the negative input terminal of differential amplifier 310 and thereby subtracted from the other input signal. This difference signal is Vpedestal-Vbackground at the output of amplifier 310. Thus, the background corrected pedestal voltage is supplied to the differentiator circuit portion.

In the meantime, at time T3, sample and hold circuit SHA3 is turned ON. That is, switch SW3 is activated so that the output signal from differential amplifier 320 is sampled and stored. Shortly thereafter, at time T4, sample and hold circuit SHA3 is turned OFF and sample and hold circuit SHA2 is turned ON concurrently. Thus, the output signal Voutput is supplied to the utilization device 350 while differential amplifier 320 operates to subtract Vpedestal (corrected) at sample and hold circuit SHA2 from the representative signal Vpedestal (corrected) supplied by amplifier 310 during time T4 to T5.

At time T5, the LED 101 is turned OFF (as are sample and hold circuits SHA2 and SHA3) while sample and hold circuit SAH1 is turned ON. The sequence can then be repeated under control of the timing generator 360 which also provides a synchronizing signal SYNC to the utilization device 360.

When Vpedestal (corrected) has stablized, the output of differential amplifier 320 is sampled by sample and hold SHA3. The value held in sample and hold SAH2 corresponds to the previous voltage of Vpedestal (corrected). The value held in sample and hold SHA3 is the derivative of the signal. After the output value has been held, sample and hold SHA3 is updated with the current value of Vpedestal to be used for the next sample.

This sequence of signals assures a clean, clear reading of the modulated signal at the detector site is achieved. The output signal is expressed as:

$$Voutput=A*(V[N]-V[N-1])$$

where A is a gain constant; V[N] is the current background corrected photo-diode voltage; V[N−1] is the previous background-corrected photo-diode voltage which occurs at time $\Delta T$ where, and $\Delta T$ is the time between samples. The operation of subtracting the previous corrected pedestal value from the current pedestal value with a known time interval $\Delta T$ between samples produces the discrete time derivative of the signal ($\Delta V/\Delta T$).

The gain constant A is determined by the several amplifiers in the system. The current, and prior, voltages are obtained by the proper sequencing of the signals applied to the several sample and hold circuits.

Incidentally, by maintaining the "sample" signals as narrow as possible, power consumption in the system is kept at a minimum. Moreover, in an alternative embodiment, Voutput can be converted into a digitized signal (see FIG. 2C) for further operations.

Thus, there is shown and described a unique design and concept of near infra-red signal processing system. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A signal processing system comprising, signal detector means for producing electrical signals representative of the detection of a signal by said signal detection means, first sample and hold means connected to said signal detector means to selectively sample and hold said electrical signals, first differential amplifier means connected to said signal detector means and to said first sample and hold means and operative to produce a corrected signal representative of the difference between the electrical signals produced by said signal detector means and the signal selectively held in said first sample and hold means, second sample and hold means connected to the output of said first differential amplifier means to selectively sample and hold said corrected signal, second differential amplifier means connected to the output of said first differential amplifier means and to said second sample and hold means and operative to produce a signal representative of the difference between the signals produced by said first differential amplifier means and said second sample and hold means, third sample and hold means connected to the output of said second differential amplifier means to selectively produce an output signal representative of the difference between the signals produced by said second differential amplifier means and said second sample and hold means, and timing control means connected to each of said first, second and third sample and hold means to control the operations thereof.

2. The system recited in claim 1 wherein, said signal detector means includes a transimpedance amplifier means for amplifying said electrical signal.

3. The system recited in claim 1 wherein, each of said first, second and third sample and hold means includes, switching means controlled by said timing control means, energy storing means selectively energized via said switching means, and amplifying means connected to receive a signal from said energy storing means.

4. The system recited in claim 3 wherein, said energy storing means comprises capacitor means.

5. The system recited in claim 3 wherein, the respective switching means included in each of said first, second and third sample and hold means is activated by said timing control means at different times relative to each other.

6. The system recited in claim 1 wherein, said timing control means activates said first sample and hold means while said signal detector means is not activated.

7. The system recited in claim 6 wherein, said timing control means activates said second and third sample and hold means in sequence while said first sample and hold means is not activated.

8. The system recited in claim 1 wherein, said signal detector means includes a photodetector means for producing an electrical signal in response to an optical signal.

9. The system recited in claim 8 wherein, said signal detector means includes a light emitting diode.

10. The system recited in claim 1 wherein, said signal detector means includes an illuminating device for selectively providing an optical signal.

11. The system recited in claim 10 wherein, said illuminating means comprises a light emitting diode (LED).

12. The system recited in claim 10 wherein, said optical signal is in the near infra-red range.

13. The system recited in claim 1 including, amplifier means connected from said signal detector to said first sample and hold means and to said first differential amplifier means to amplify said electrical signals.

14. A heart pulse rate detector comprising, an optical sensor adapted to be mounted adjacent to a blood vessel in the body of a user to sense heart pulses in said blood vessel, said optical sensor operative to produce a background signal in the absence of a heart pulse in said blood vessel and a pedestal signal in response to the sensing of a heart pulse;

first sample and hold means connected to said optical sensor to selectively sample and hold said background signal, first differential amplifier means connected to said optical sensor and to said first sample and hold means and operative to produce a corrected signal representative of the difference between said pedestal signal produced by said optical sensor and the background signal selectively held in said first sample and hold means, second sample and hold means connected to the output of said first differential amplifier means to selectively sample and hold said corrected signal, second differential amplifier means connected to the output of said first differential amplifier means and to said second sample and hold means and operative to produce a signal representative of the difference between the signals produced by said first differential amplifier means and said second sample and hold means, third sample and hold means connected to the output of said second differential amplifier means to selectively produce an output signal representative of the difference between the signals produced by said second differential amplifier means and said second sample and hold means, and timing control means connected to each of said first, second and third sample and hold means to control the operations thereof.

15. The heart pulse rate detector recited in claim 14 including, light emitting means adapted to be mounted adjacent to said optical sensor and to selectively provide illumination thereto.

16. The detector recited in claim 14 wherein, said signal detection means includes an amplifier connected from said optical sensor to said first sample and hold means and to said first differential amplifier means.

17. The detector recited in claim 16 wherein, said amplifier comprises a transimpedance amplifier.

18. The detector recited in claim 14 wherein, said optical sensor includes a light emitting device and a light detecting device, said light emitting device is connected to and selectively activated by said timing control means.

19. A signal processing system comprising, signal detector, first sample and hold circuit connected to said signal detector, first connecting circuit, first differential amplifier connected to said signal detector via said first connecting circuit and to said first sample and hold circuit and operative to produce a corrected signal representative of the difference between the signals produced by said signal detector and said first sample and hold circuit, second sample and hold circuit connected to the output of said first differential amplifier, second connecting circuit, second differential amplifier connected to the output of said first differential amplifier via said second connecting circuit and to said second sample and hold circuit and operative to produce a signal representative of the difference between the signals produced by said first differential amplifier and said second sample and hold circuit, third sample and hold circuit connected to the output of said second differential amplifier to selectively produce an output signal representative of the difference between the signals produced by said second differential amplifier and said second sample and hold circuit, and timing controller connected to each of said first, second and third sample and hold circuit to control the operations thereof.

20. The system recited in claim 19 wherein, each of said first and second connecting circuits comprises a voltage divider circuit.

* * * * *